US007090987B1

(12) United States Patent
Nixon et al.

(10) Patent No.: US 7,090,987 B1
(45) Date of Patent: Aug. 15, 2006

(54) METHODS FOR THE IDENTIFICATION OF COMPOUNDS FOR THE TREATMENT OF NEURONAL ATROPHY-ASSOCIATED DEMENTIA

(76) Inventors: Ralph A. Nixon, One Hillside Pl., Tarrytown, NY (US) 10591; Anne M. Cataldo, 29 Normandy Village, Apt. 1, Nanuet, NY (US) 10954; Paul M. Mathews, 10 Home Pl., Irvington, NY (US) 10533

( * ) Notice: Subject to any disclaimer, the term of this patent is extended or adjusted under 35 U.S.C. 154(b) by 0 days.

(21) Appl. No.: 09/561,582

(22) Filed: Apr. 28, 2000

Related U.S. Application Data

(60) Provisional application No. 60/140,643, filed on Jun. 23, 1999, provisional application No. 60/140,644, filed on Jun. 23, 1999, provisional application No. 60/131,890, filed on Apr. 30, 1999, provisional application No. 60/131,991, filed on Apr. 30, 1999.

(51) Int. Cl.
*C12Q 1/00* (2006.01)
*G01N 33/53* (2006.01)

(52) U.S. Cl. .............................. 435/7.2; 435/4; 435/7.1

(58) Field of Classification Search .................... 435/4, 435/325; 436/536, 518
See application file for complete search history.

(56) References Cited

U.S. PATENT DOCUMENTS

| 5,028,622 | A | 7/1991 | Plaitakis et al. |
| 5,538,983 | A | 7/1996 | Buxbaum et al. |
| 5,686,269 | A | 11/1997 | Nixon et al. |

FOREIGN PATENT DOCUMENTS

| EP | 0652 012 A | 5/1995 |
| WO | WO 97/44668 | 11/1997 |
| WO | WO 98/21589 | 5/1998 |
| WO | WO 98/40484 | 9/1998 |

OTHER PUBLICATIONS

Zhao et al., J. of Neuroscience Res., Feb. 1, 1995, 40(2):261.*
ATCC web catalog ATCC No. CRL-1721, Rattus norvegticuss PC-12.*
Frautschy et al., J. Neurosci., Oct. 15, 1998, 18(20):8311-21.*
Tsuzuki et al., Brain Research, 1994, 659:213-220.*
Bjarnadottir et al., "Intracellular Accumulation of the Amyloidogenic L68Q Variant of Human Cystatin C in NIH/3T3 Cells," Journal of Clinical Pathology: Molecular Pathology 51:317-326 (1998).
Busca et al. "The Carboxy-Terminal Region of Human Lipoprotein Lipase is Necessary for its Exit From the Endoplasmic Reticulum," Journal of Lipid Research 39:821-833 (1998).

Cataldo et al., "Increased Neuronal Endocytosis and Protease Delivery to Early Endosomes in Sporadic Alzheimer's Disease: Neuropathologic Evidence for a Mechanism of Increased β-Amyloidogenesis," Journal of Neuroscience 17:6142-6151 (1997).
Cataldo et al., "Lysosomal Hydrolases of Different Classes are Abnormally Distributed in Brains of Patients with Alzheimer Disease," Proceedings of the National Academy of Sciences (USA) 88:10998-11002 (1991).
Cataldo et al., "Lysosomal Abnormalities in Degenerating Neurons Link Neuronal Compromise to Senile Plaque Development in Alzheimer Disease," Brain Research 640: 68-80 (1994).
Cataldo et al., "Properties of the Endosomal-Lysosomal System in the Human Central Nervous System: Disturbances Mark Most Neurons in Populations at Risk to Degenerate in Alzheimer's Disease," Journal of Neuroscience 16:186-199 (1996).
Dash et al., "Inhibitors of Endocytosis, Endosome Fusion, and Lysosomal Processing Inhibit the Intracellular Proteolysis of the Amyloid Precursor Protein," Neuroscience Letters 164:183-186 (1993).
Granholm et al., "Segmental Trisomy Ts65Dn Mice Have a Decrease in Nerve Growth Factor Receptors in Septal Forebrain Neurons," Abstracts, Society for Neuroscience 24:2008, Abstract 803.4 (1998).
Haass et al., "Targeting of Cell-Surface β-Amyloid Precursor Protein to Lysosomes: Alternative Processing into Amyloid-Bearing Fragments," Nature 357:500-503 (1992).
Holtzman et al., "Developmental Abnormalities and Age-Related Neurodegeneration in a Mouse Model of Down Syndrome," Proceedings of the National Academy of Sciences (USA) 93:13333-13338 (1996).
Ikegami et al., "Immunohistochemical Examination of Phosphorylated Tau in Granulovacuolar Degeneration Granules," Psychiatry and Clinical Neurosciences 50: 137-140 (1996).
Korenberg, "Mental Modelling," Nature Genetics 11:109-111 (1995).
Punnonen et al., "Effects of Vinblastine, Leucine, and Histide, and 3-Methyladenine on Autophagy in Ehrlich Ascites Cells," Experimental & Molecular Pathology 52:87-97 (1990).

(Continued)

*Primary Examiner*—Sharon Turner
(74) *Attorney, Agent, or Firm*—Kristina Bieker-Brady; Clark & Elbing LLP

(57) ABSTRACT

The invention features methods of diagnosing and treating a patient having Alzheimer's disease or other neuronal atrophy-associated dementia by determining or altering, respectively, the level of activity of pathways from the endoplasmic reticulum to lysosomes in the patient.

5 Claims, 11 Drawing Sheets

OTHER PUBLICATIONS

Reeves et al., "A Mouse Model for Down Syndrome Exhibits Learning and Behaviour Deficits," Nature Genetics 11:177-183 (1995).

Watari et al., "Niemann-Pick C1 Protein: Obligatory Roles for N-Terminal Domains and Lysosomal Targeting in Cholesterol Mobilization," Proceedings National Academy Sciences 96:805-810 (1999).

Yan Zhou et al., "A Mutation in a Mild Form of Galactosialidosis Impairs Dimerization of the Protective Protein and Renders it Unstable," EMBO Journal 10:4041-4048 (1991).

U.S. Appl. No. 09/560,124, filed Apr. 28, 2000, Ralph Nixon.

Bucci et al., The Small GTPase rab5 Functions as a Regulatory Factor in the Early Endocytic Pathway, Cell 70:715-28, 1992.

Stenmark et al., Inhibition of rab5 GTPase Activity Stimulates Membrane Fusion in Endocytosis, EMBO Journal 13:1287-1296, 1994.

Stenmark et al., Rabaptin-5 is a Direct Effector of the Small GTPase Rab5 in Endocytic Membrane fusion, Cell 83:423-32, 1995.

Anglade et al., "Apoptosis and Autophagy in Nigral Neurons of Patients with Parkinson's Disease," Histol. Histopathol. 12:25-31 (1997).

Bernstein et al., "Lysosomal Proteinases as Putative Diagnostic Tools in Human Neuropathology; Alzheimer Disease (AD) and Schizophrenia," ACTA Histochem. Suppl. 42:19-24 (1992).

Guo et al., "Alzheimer's Presenilin Mutation Sensitizes Neural Cells to Apoptosis Induced by Trophic Factor Withdrawal and Amyloid β-Peptide: Involvement of Calcium and Oxyradicals," J. Neurosci. 17:4212-4222 (1997).

Soustek et al., "Autolysosomes in Alzheimer's Disease and Their Possible Role in its Pathogenesis; An Ultrastructural Study," Zentralbl. Pathol. 140: 143-148 (1994).

* cited by examiner

METHODS FOR THE IDENTIFICATION OF COMPOUNDS FOR THE TREATMENT OF NEURONAL ATROPHY-ASSOCIATED DEMENTIA

CROSS-REFERENCE TO RELATED APPLICATIONS

This application claims benefit to U.S. Provisional Application Nos. 60/131,890, filed Apr. 30, 1999, 60/131,991, filed Apr. 30, 1999, 60/140,643, filed Jun. 23, 1999, and 60/140,644, filed Jun. 23, 1999, each hereby incorporated by reference.

STATEMENT AS TO FEDERALLY SPONSORED RESEARCH

The invention was supported in part by National Institutes of Health grant AG 10916. The government has certain rights to the invention.

BACKGROUND OF THE INVENTION

The invention relates to methods of identifying compounds for the treatment of Alzheimer's disease (AD) and non-AD neuronal atrophy-associated dementia.

Rare early-onset forms of familial Alzheimer's disease (FAD) are inherited as autosomal dominant diseases. Mutations in the broadly expressed transmembrane amyloid precursor protein (APP), although extremely rare, were the first FAD-causing genetic defects identified and are associated with abundant cerebrovascular β-amyloid, a major neuropathological feature of AD. All of these mutations appear to influence the proteolytic processing of APP, modifying the amount of and/or length of the Aβ peptide, the major component of β-amyloid. Mutations of the presenilin genes (PS1 and PS2) were more recently identified as causing more than half of all cases of early-onset FAD. Among other proposed effects, presenilin mutations influence the production of the 42 and 40 kDa forms of Aβ1(Aβ1-42 and Aβ1-40) by favoring the former. The existing animal models of AD, other than aged primates or dogs, make use of mutant APP and mutant presenilin to create mice that deposit β-amyloid.

An early hallmark of AD pathology is activation of the lysosomal system (LS)(Cataldo et al., Neuron 14:671–680, 1995; Nixon et al., Trends Neurosci. 18:489–496, 1995; Cataldo et al., Adv. Exp. Med. Biol. 389:271–280, 1996; Cataldo et al., J. Neurosci. 16:186–199, 1996). Despite concerted efforts, there is an incomplete understanding of the mechanism of LS activation and its role in AD pathogenesis.

Thus, there is a need to define the pathogenic significance of the early and progressive activation of the LS in neuronal atrophy-associated dementias such as AD. There is also a need for assays for compounds that are useful for the treatment of neuronal atrophy-associated dementias, and particularly for compounds that reduce Aβ formation. Moreover, there is a need for better tools for the diagnosis of neuronal atrophy-associated dementias.

SUMMARY OF THE INVENTION

In a first aspect, the invention features a method of diagnosing Alzheimer's disease or other neuronal atrophy-associated dementia in a human patient, the method including determining the level of activity of pathways from the endoplasmic reticulum to lysosomes in the patient, and comparing the level of the activity to normal levels, wherein an increase in the level of activity relative to normal indicates AD or other neuronal atrophy-associated dementia.

In one embodiment, the measuring includes measuring the level of activity of pathways from the endoplasmic reticulum to lysosomes in a cell of the patient. Preferably the cell is a neuron, a fibroblast, or an endothelial cell. In a related embodiment, the measuring includes measuring the level of activity of pathways from the endoplasmic reticulum to lysosomes in a biological fluid of the patient.

In a second aspect, the invention features a method for identifying a candidate compound as a compound that is useful for the treatment of AD or other neuronal atrophy-associated dementia. The method includes: a) providing a cell; b) contacting the cell with the candidate compound; and c) determining the activity of pathways from the endoplasmic reticulum to lysosomes, wherein a decrease in the activity, relative to the activity in a control cell not contacted with the candidate compound, identifies the candidate compound as a compound that is useful for the treatment of AD or other neuronal atrophy-associated dementia.

In a third aspect, the invention features a method for identifying a candidate compound as a compound that is useful for the treatment of AD or other neuronal atrophy-associated dementia. The method includes: a) providing a cell; b) contacting the cell with a candidate compound that decreases the activity of pathways from the endoplasmic reticulum to lysosomes; and c) determining the ability of the cell to withstand cytotoxic challenge such as, but not limited to, oxidative stress, Aβ, hypoxia, or metabolic challenge, wherein an increase in cell survival in a cell contacted with the compound, relative to survival of a cell not contacted with the compound, identifies the compound as one that is useful for the treatment of AD or other neuronal atrophy-associated dementia.

In a fourth aspect, the invention features another method for identifying a candidate compound as a compound that is useful for the treatment of AD or other neuronal atrophy-associated dementia. The method includes: a) providing a cell; b) contacting the cell with a candidate compound that decreases the activity of pathways from the endoplasmic reticulum to lysosomes; and c) determining the levels of Aβ produced by the cell, wherein a decrease produced by a cell contacted with the compound compared to a control cell not contacted with the candidate compound identifies the candidate compound as a compound that is useful for the treatment of AD or other neuronal atrophy-associated dementia.

In preferred embodiments of the second, third, or fourth aspect, the cell is in a human or a mouse, or is from a human or a mouse. The cell may contain a polypeptide sequence including a mutation that is present in a human with familial AD. In various preferred embodiments, the polypeptide sequence includes PS1 or PS2, and the mutation is P117L, M146L, M146V, S169L, M233T, or A246G, or the polypeptide includes APP. The cell can be in vitro. The cell can be, for example, a fibroblast, an endothelial cell, or a neuron.

The cell can be in an animal, such as a mouse, rat, dog, cat, or monkey, or the cell can be in culture. The cell can be, for example, a fibroblast, an endothelial cell, or a neuron. In one embodiment, the autophagy inhibitor is leupeptin.

In a fifth aspect, the invention features a method for treating a patient with AD or other neuronal atrophy-associated dementia, the method including administering to the patient a compound that decreases the activity of pathways from the endoplasmic reticulum to lysosomes.

In various embodiments, the patient has sporadic AD, familial AD, Down's syndrome (DS), Parkinson's disease, or has a mutation in their PS1 gene, their PS2 gene, or their APP gene.

Preferred compounds are 3-methyladenine (3MA), a derivative of 3MA, leucine, histidine, and vinblastine. Preferably, the compound further reduces Aβ formation.

In all of the foregoing aspects of the invention, the preferred neuronal atrophy-associated dementia is AD.

By "pathways from the endoplasmic reticulum to lysosomes" is meant the autophagy pathway and the pathway for the direct conversion of ER to lysosome. Activity of these pathways can be measured using methods described herein. A decrease or a reduction in the activity of pathways from the endoplasmic reticulum to lysosomes is any diminishment of the activity relative to a control cell. Preferably, the decrease in activity is at least 5%, more preferably 10%, and most preferably 25% or even 50%. The percent change is usually measured for a period of hours or days, but can be measure in terms of weeks or even longer.

By "dementia" is meant deterioration of intellectual faculties, such as memory, concentration, and judgment, resulting from an organic disease or a disorder of the brain. By "neuronal atrophy-associated dementia" is meant dementia caused by a loss in neurons and includes dementia associated with AD, Parkinson's disease, frontotemporal dementia, DS, and amyolateral sclerosis (ALS).

By "metabolic challenge" is meant exposure of a cell to conditions which are generally toxic or harmful to the cell, including disruption of calcium homeostasis, trophic factor deprivation, glucose or amino acid starvation, hypoxia, excitotoxic challenge, and disruption of a cellular proteolytic system such as the lysosomal system.

The invention provides methods for identifying drugs useful for the treatment or prevention of AD or other neuronal atrophy-associated dementia. Additionally, the invention provides new drug targets for rational drug design. Also provided by the invention are compounds that may be useful for the treatment or prevention of AD or other neuronal atrophy-associated dementia.

Other features and advantages of the invention will be apparent from the following description of the preferred embodiments thereof and from the claims.

DETAILED DESCRIPTION OF THE INVENTION

Figure 1:
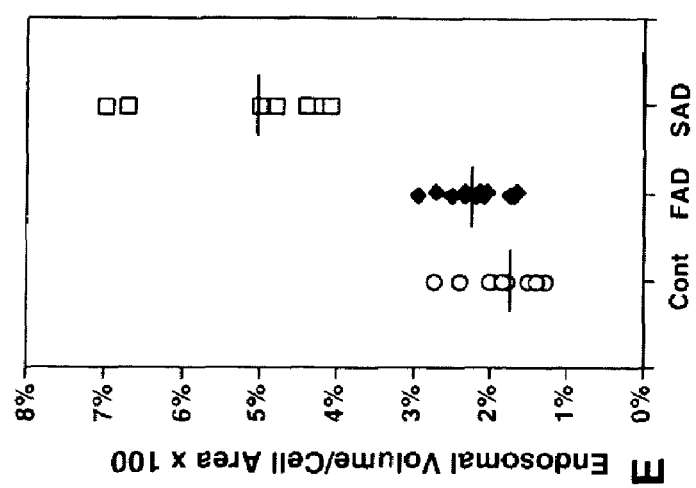
FIGS. 1A–1D are a series of photographs showing abnormally large rab5-immunopositive early endosomes in pyramidal neurons from individuals with sporadic AD (arrow in FIG. 1B) when compared to controls (FIG. 1A). Enlarged early endosomes were not seen in individuals with PS mutations (FIG. 1C) despite high levels of β-amyloid deposition (FIG. 1D, arrowheads).
FIG. 1E is a graph showing that the average endosomal volume per neuron in the PS-FAD cases was similar to that of normal controls (control mean, 1.88%; PS-FAD mean, 2.20%; SAD mean, 5.04%).
Figure 1:
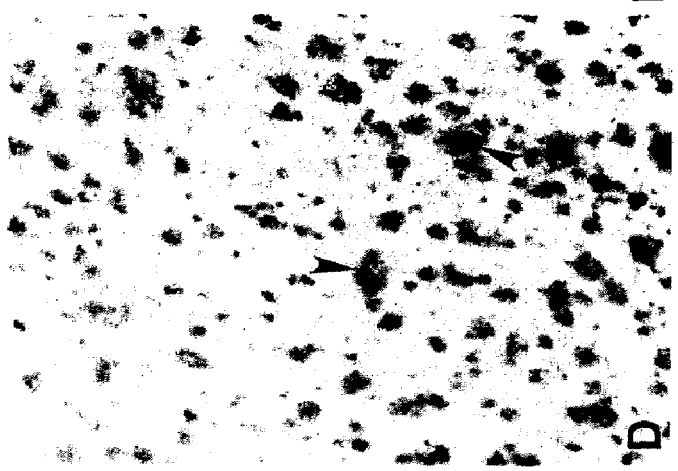
Figure 1:
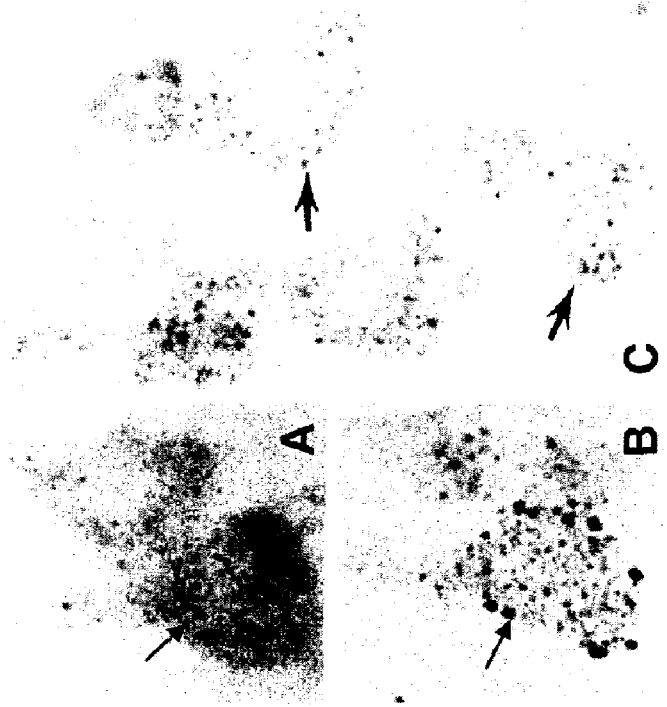

We have discovered that two non-endosomal routes to the lysosome play a significant role in LS activation in AD, particularly in PS-FAD. This discovery allows for (i) the identification of compounds that are useful for the treatment of AD by assessing their ability to decrease LS activity originating from the endoplasmic reticulum to lysosomes; (ii) the diagnosis of AD based on assays that measure activity of pathways from the endoplasmic reticulum to lysosomes; and (iii) treatment of AD with drugs that decrease the activity of pathways from the endoplasmic reticulum to lysosomes (e.g., 3MA, leucine, histidine, or vinblastine).

One of the two routes is autophagy, the process by which cells digest their own cytoplasm to provide materials for new synthesis (Seglen et al., Semin. Cell Biol. 1:441–448, 1990). Based on studies in non-neural tissues, autophagy begins with a rate-limiting sequestration of cytoplasm in a membranous organelle (phagophore) of unknown origin and composition, but believed to be derived from ER membranes. The vacuole eventually formed (autophagosome) may fuse with a prelysosomal compartment, likely to be the late endosome. Autophagy plays a critical role in modulating cellular protein economy and remodeling cell architecture in response to physiological and pathological stimuli (Brunk et al., Mutat. Res. 275:395–403, 1992; Dunn, J. Cell Biol. 110:1923–1933, 1990; Cataldo and Nixon, Trends Neurosci. 18:489–496, 1995; Seglen et al., Semin. Cell Biol. 1:441–448, 1990). Moreover, regulated autophagy is a key mechanism by which cells control their size (Cataldo and Nixon, Trends Neurosci. 18:489–496, 1995). This function may be particularly relevant to the issue of cell atrophy as a neuropathological feature and antecedent to neurodegeneration in AD (McEwen, Mol. Psychiatry 2:255–262, 1997; Tan et al., J. Neurochem. 71:95–105, 1998). Under conditions of stress, such as amino acid deprivation in hepatocytes, autophagy may account for three-quarters of the cell's protein degradation (Mortimore and Schworer, Nature 270: 174–176, 1977; Seglen et al., Semin. Cell Biol. 1:441–448, 1990). In this situation, autophagy leads to rapid degradation of the cytosol, loss of cellular volume, and cell death within 24 hours (Schwarze and Seglen, Exp. Cell Res. 157:15–28, 1985; Seglen et al., Toxicol. Pathol. 14:342–348, 1986). In this regard, an uncommon "autophagic" neuronal cell death pattern, resembling the pattern in AD, has been described as possibly representing a variant of programmed cell death with a protracted timecourse (Clarke, Anat. Embryol. 181: 195–213, 1990; Homung et al., J. Comp. Neurol. 283: 425–437, 1989).

Little has been known about autophagy in neurons. We have discovered, however, that expression of mutant PS1 in cultured cells and in transgenic mice substantially increases autophagy.

Results from the foregoing models also suggest that another pathway to lysosomes, which is non-endosomal and non-autophagic, may be upregulated in PS-FAD. Direct conversion of ER to lysosomes was described by Noda and Farquhar (J. Cell Biol. 119:85–97, 1992) in stimulated thyroid hormone-secreting cells. This little-known pathway is especially interesting because of presenilin's predominant ER localization and the suspected impact of presenilin mutations on the proteolysis of APP within the ER or very close to the ER (Chyung et al., J. Cell Biol. 138:671–680, 1997; Cook et al., Proc. Natl. Acad. Sci. USA 93:9223–9228, 1996; Hartmann, J. Biol. Chem. 272:14505–14508, 1997; Xia et al., Golgi Biochem. 37:16465–16471, 1998).

Changes in the Endocytic Pathway and Lysosomal System in Sporadic Alzheimer's Disease Activation of the lysosomal system, evidenced by increased cathepsin gene expression and accumulation of secondary and tertiary lysosomes, is a distinctive response of neurons in sporadic AD (SAD) and DS and an early marker of metabolic dysfunction in neurons of all vulnerable cell populations in AD (Cataldo et al., Neuron 14:671–680, 1995; Cataldo et al., J. Neuropathol. Exp. Neurol. 55:704–715, 1996; Cataldo et al., Adv. Exp. Med. Biol. 389:271–280, 1996; Cataldo et al., Brain Res. 640:68–80, 1994; Nixon et al., Alzheimer's Disease, in: Advances in Clinical and Basic Research. pp 441–450, 1993). By quantitative image analysis, ~90% of neocortical perikarya in layers III and V of AD brains that demonstrate moderate-severe neuropathology contained 2- to 8-fold elevated numbers of secondary and tertiary hydrolase-positive lysosomes in the absence of chromatolytic or neurofibrillary changes (Cataldo et al., J. Neurosci. 16:186–199, 1996). In situ hybridization analysis showed the expression of cathepsin D (Cat D) mRNA to be increased 2-to 3-fold in this cell population in parallel to increases in hydrolase immunoreactivity ($p<0.0001$) (Cataldo et al., Neuron 14:671–680, 1995). Immunoreactivity levels for at least eight different lysosomal hydrolases in neurons were found to be elevated. Changes in the relative proportions of mannose-6-phosphate receptors (MPR) within affected neurons suggest that certain lysosomal hydrolases may also be misdirected to compartments that normally have low hydrolase levels. In SAD, MPR46, but not MPR215 immunoreactivity is elevated, while in PS-FAD both are increased (Cataldo et al., J. Neurosci. 17:6142–6151, 1997; Nixon et al., Sixth International Conference on Alzheimer's Disease. Vol. 19, Amsterdam, pp S136, 1998). Neurons exhibiting overt atrophy or neurofibrillary changes display robust accumulation of hydrolase-positive lysosomes and lipofuscin, which are then released into the extracellular space following cell lysis (Cataldo et al., Brain Res. 640 68–80, 1994; Cataldo and Nixon, Proc. Natl. Acad. Sci. USA, 87:3861–3865, 1990; Cataldo et al., Proc. Natl. Acad. Sci. USA 88:10998–11002, 1991). These lysosomal compartments, containing a full battery of enzymatically competent hydrolases, persist in the extracellular space specifically in association with deposits of β-amyloid within both senile and diffuse plaques (Cataldo et al., J. Neuropath. Exp. Neurol. 55:704–715, 1996; Cataldo et al., Brain Res. 640:68–80, 1994; Cataldo and Nixon, Proc. Natl. Acad. Sci. USA 87:3861–3865, 1990; Cataldo, et al., Proc. Natl. Acad. Sci. USA. 88:10998–11002, 1991). Cat D content was >3-fold higher in ventricular CSF from AD patients (n=35) than from 26 patients with Huntington's, diffuse Lewy body, or Pick's disease ($p<0.001$), indicating that Cat D release from affected neurons is an active ongoing process (Schwagerl et al., J. Neurochem. 64:443–446, 1995). As cells degenerate, the persistence of hydrolase-laden compartments in the extracellular space is a unique feature of AD. Extracellular accumulations of lysosomal hydrolases have been observed only in brains of patients with AD or other conditions where β-amyloid accumulates.

Figure 2:
FIGS. 2A–2C are a series of photographs showing cathepsin D immunoreactivity. Similar to the SAD brain (FIG. 2B), PS-FAD brain (FIG. 2C) displayed denser cathepsin D immunoreactivity in pyramidal neurons in cortical laminae III and V compared to controls (FIG. 2A). In contrast to SAD, cathepsin D immunolabeling in PS-FAD was also increased in neurons of laminae II and IV of the prefrontal cortex. Senile plaques (arrowheads) displayed Cat D immunoreactivity.

Accentuation of Lysosomal System Upregulation without Endosomal System Alterations in Human Alzheimer's Disease Brains Carrying Presenilin Mutations We have found that pyramidal neurons in individuals with moderate to severe AD caused by PS1 mutations do not display the early endosomal abnormalities seen in SAD and DS (FIG. 1). That PS mutations do not alter endosomal function is consistent with recent evidence that ApoE genotype does not affect the onset or severity of AD neuropathology associated with PS-FAD (Cruts and Van Broeckhoven, Ann. Med. 30:560–565, 1998), and that PS effects on Aβ overproduction may be exerted in part via an ER-LS pathway rather than via an endocytic pathway (EP). In contrast to the normal-appearing early endosomes in PS-FAD brains, we observed a substantial upregulation in the numbers of lysosomes (FIG. 2). By Cat D and Cat B immunocytochemistry, we found that the LS activation in the PS-FAD brains was greater than in SAD. Neuronal populations that are less vulnerable in AD, such as those in lamina II and IV of prefrontal cortex, showed marked lysosomal upregulation in PS-FAD but not SAD.

Lysosomal System Abnormalities in $PS1_{M146L}$/APPswe Transgenic Mice

Figure 3:
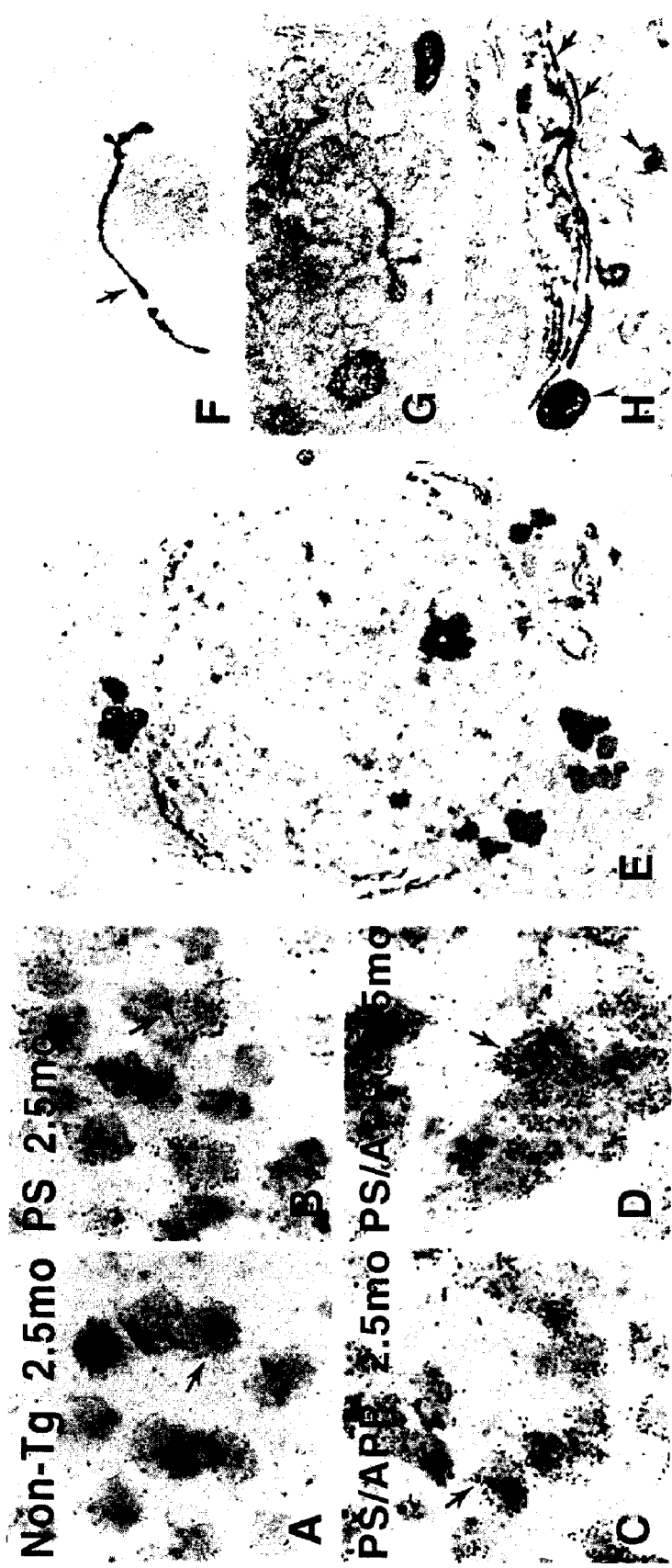
FIGS. 3A–3D are a series of photographs showing lysosomal system upregulation, as revealed by LAP enzyme cytochemistry, in $PS1_{M146L}$ mice (FIG. 3B) and $PS1_{M146L}$/APPswe transgenic mice (FIGS. 3C and 3D) when compared to a non-transgenic mouse (FIG. 3A).
FIGS. 3E–3H are photographs of LAP enzyme cytochemistry in control mice (FIG. 3F), $PS1_{M146L}$/APPswe transgenic mice (FIGS. 3E and 3H), and $PS1_{M146L}$ mice (FIG. 3G) at the electron microscope level, again showing upregulation of the lysosomal system in the transgenic mice.
Figure 4:
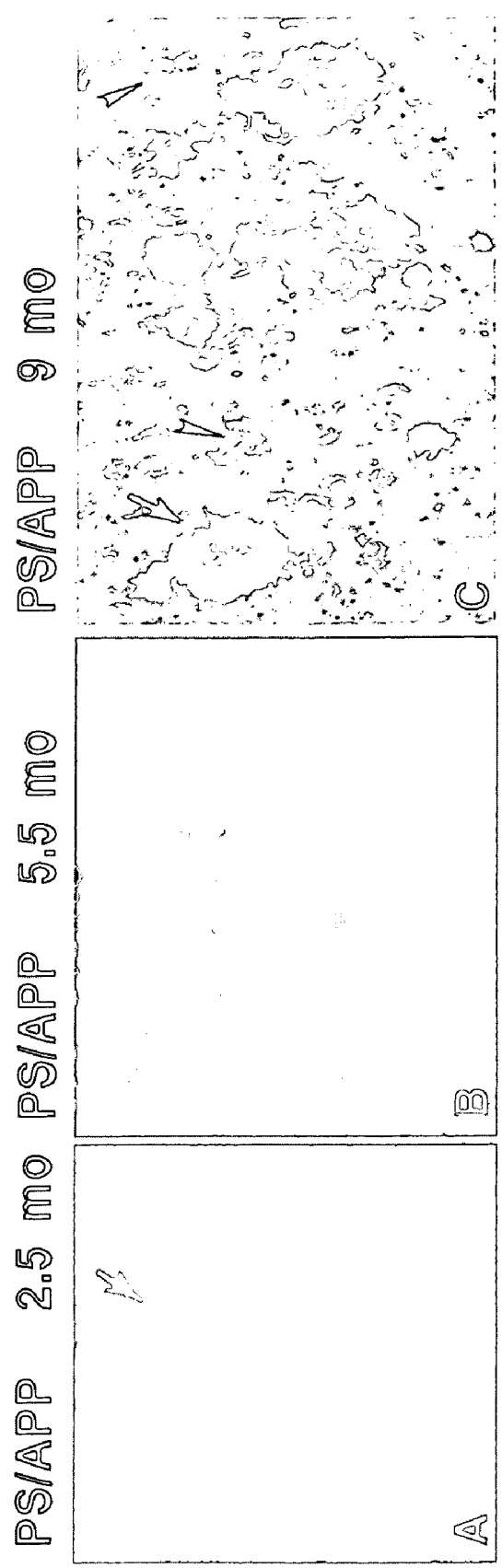
FIGS. 4A–4C are a series of photographs showing the association of a biotinylated sMPR probe with Aβ-containing plaques in $PS1_{M146L}$ APPswe transgenic mice.

We have found that many of the same characteristics of LS activation that are seen in AD are also seen in transgenic mice expressing $PS1_{M146L}$ and/or APPswe (Duff et al., Nature 383:710–713, 1996). Like human PS-FAD cases, these transgenic mice do not show abnormally large early endosomes. We have shown that mice expressing APPswe, like AD subjects, have increased intracellular accumulation of lysosomal proteases, such as cathepsins D and B, as well as the non-proteolytic enzyme lysosomal acid phosphatase (LAP), when compared to control littermates. This lysosomal upregulation in APPswe transgenic mice was found at five months of age, prior to plaque deposition. $PS1_{M146L}$ mice, which do not develop plaques, also show LS activation, although in a restricted population of neurons that appears to overlap with the highest levels of PS1 transgene expression (FIG. 3). Both the early appearance of lysosomal changes in the APPswe transgenic mice and the appearance of lysosomal changes in the $PS1_{M146L}$ mice indicate that LS upregulation may occur without β-amyloid deposition. Introduction of both transgenes potentiates the LS abnormalities and hastens and exacerbates neuropathology (FIGS. 3 and 4).

Lysosomal Enzymes are Associated with Plaques in Transgenic Mice

Figure 5:
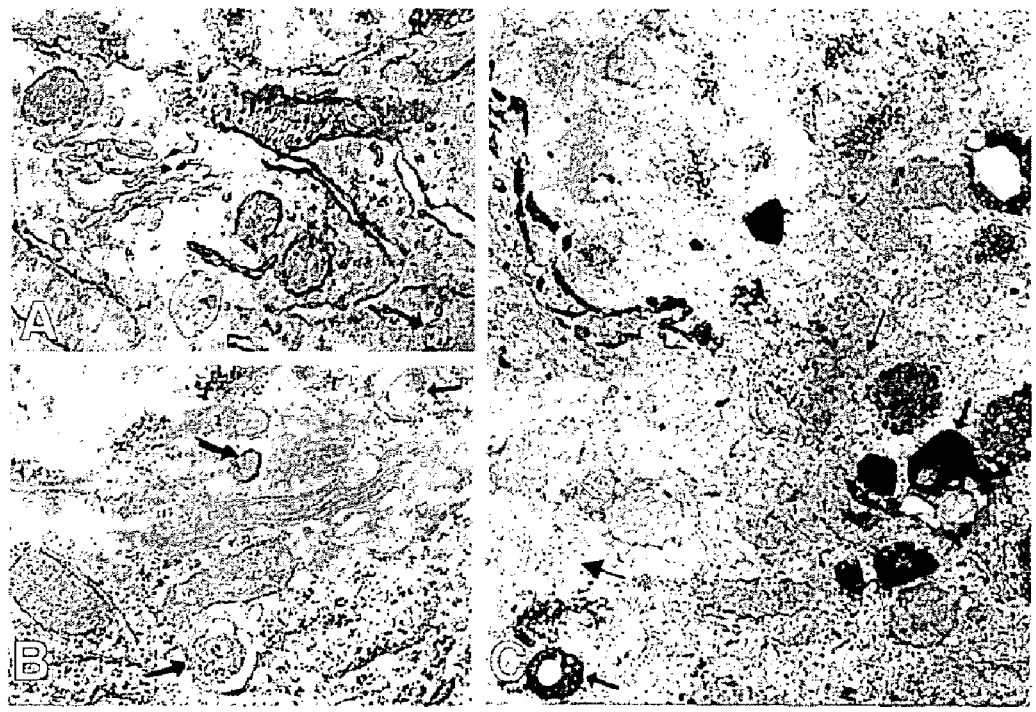
FIGS. 5A and 5B are photographs of autophagic vacuoles (arrows) in control mice (FIG. 5A) and $PS1_{M146L}$/APPswe transgenic mice (FIG. 5B).
FIG. 5C is a photograph showing autophagic vacuoles are a subset of the population containing enzyme cytochemical reaction product for acid phosphatase activity.

Lysosomal enzymes are closely associated with β-amyloid-containing senile plaques in human AD brain (Cataldo et al., J. Neuropathol. Exp. Neurol. 55:704–715, 1996; Cataldo et al. Brain Res., 640:68–80, 1994; Cataldo and Nixon, Proc. Natl. Acad. Sci. USA 87:3861–3865, 1990). Similarly, lysosomal enzymes (as detected by Cat D immunoreactivity and LAP activity), including all mannose 6-phosphate-tagged lysosomal hydrolases (shown in FIG. 4), are associated with plaques in $PS1_{M146L}$/APPswe mice and aged APPswe mice. We have now discovered that plaques in the $PS1_{M146L}$/APPswe mice contain degenerating neurites filled with autophagic vacuoles (FIG. 5). By EM, these neuritic profiles contained abundant lysosomes and autophagic vacuoles (AV) and, by LM, increased immuno-labeling for LAMP-1, a major lysosome-associated membrane protein.

Increased Autophagy in Familial Alzheimer's Disease Transgenic Mice

Our immuno- and enzyme cytochemistry and morphologic examinations at the EM level of $PS1_{M146L}$/APPswe mice support our hypothesis that increased neuronal hydrolytic activity is intimately linked to the generation of AD-like pathology. Ultrastructural studies show increased numbers of autophagic vacuoles in the $PS1_{M146L}$/APPswe mice vs. liftermate controls and in the $PS1_{M146L}$ mice vs. controls using morphologic criteria combined with LAP activity as a marker for hydrolytic compartments (FIG. 5). AVs are restrictively defined as membrane-enclosed structures in which cellular organelles or cellular contents (such as ribosomes) are identifiable (Cataldo and Nixon, Trends Neurosci. 18:489–496, 1995). Not only were the number of LAP positive lysosomes and AV increased over that seen in control mice, but in the $PS1_{M146L}$/APPswe mice, LAP activity was seen in the trans-most and medial sacules of the Golgi apparatus and frequently, albeit less often, in the cis-most saccule (compare FIG. 3F with FIG. 3H). This unusual distribution throughout the Golgi is indicative of increased LAP biosynthesis. Taken together, our data show an increase in LAP activity and increased numbers of AV within neurons of the $PS1_{M146L}$/APPswe mice, and support a model of increased lysosomal activity and autophagy via a non-endosomal route in some forms of FAD.

Increased Autophagy in Cells Expressing Presenilin-I

Figure 6:
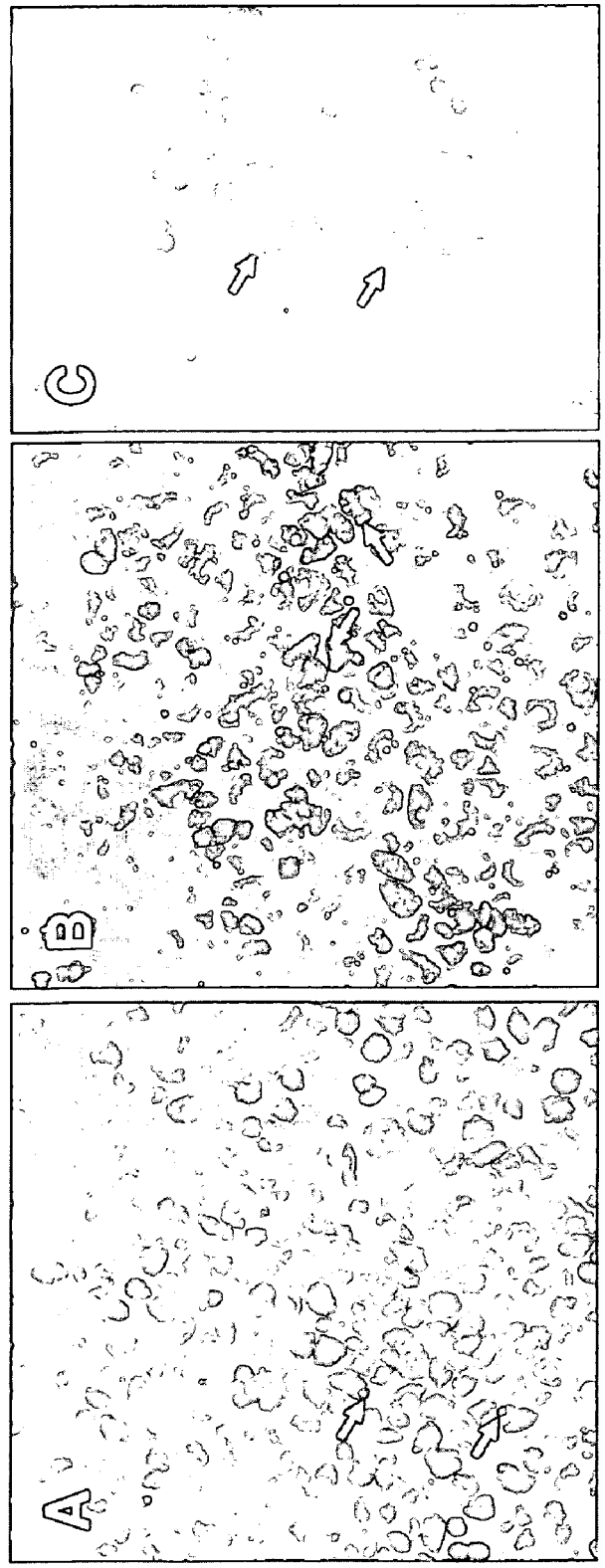
FIGS. 6A–6C are a series of photographs showing monodansyl-cadaverine labeling of autophagic vacuoles in control L cells (FIG. 6A) and $PS1_{P117L}$ transfected L cells (FIGS. 6B and 6C).

Importantly, the foregoing observations of lysosomal system activation and increased autophagy are not restricted to transgenic mice expressing mutant PS1. We generated murine L cell lines stably transfected with cDNAs expressing human wild-type PS1 as well as the $PS1_{P117L}$ mutant (Wisniewski et al., Neuroreport 9:217–221, 1998). Equivalent levels of PS1 expression following induction was confirmed using a human-specific PS1 monoclonal antibody generated in this laboratory. When living cells were labeled with monodansyl cadavcine (MDC), a greater number of MDC-positive vacuoles were seen in the L cells expressing the mutant PS1 than in L cells overexpressing wild-type PS1 (FIG. 6) or in non-transfected control cells. MDC is a specific in vivo marker for autophagic vacuoles (Biederbick et al., Eur. J. Cell Biol. 66:3–14, 1995). The increased numbers of MDC-positive, autophagic vacuoles seen in L cells expressing mutant PS1 is consistent with our conclusion that autophagy is generally increased by expression of mutant PS1 and that a disruption of autophagy is likely to play a role in the pathology of AD.

Figure 7:
FIGS. 7A–7C are a series of photomicrographs showing increased numbers of autophagic vacuoles in N2a cells expressing PS1Δ9/APPswe (arrows FIG. 7C) when compared to untransfected N2a cells (FIG. 7A) and PS1 wt/APPswe expressing N2a cells (FIG. 7B).
Figure 8:
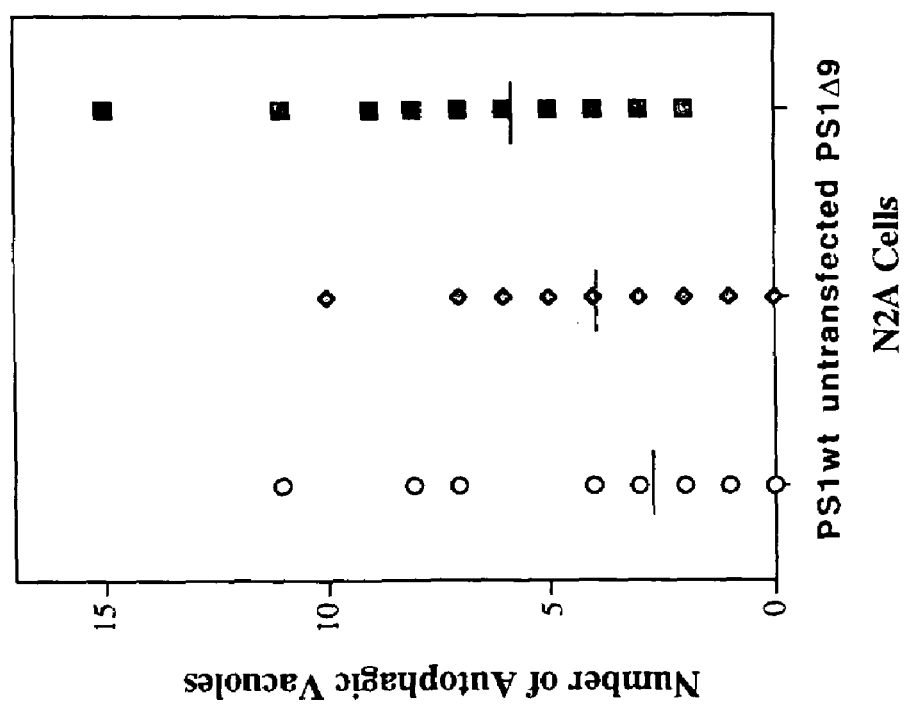
FIG. 8 is a schematic illustration showing quantitation of authophagic vaculoes in N2a cells overexpressing wild-type PS1, in untrasfected N2a cells, and in PS1Δ9 expressing N2a cells.

We have corroborated these observations in a neuronal-like cell, murine N2a cells (FIG. 7). Autophagic vacuoles were identified by EM ultrastructural morphology in N2a cells overexpressing wild-type PS1, in untransfected cells, and in cells expressing the exon 9 deletion of PS1 (PS1Δ9) (Perez-Tur et al., Neuroreport 7:297–301, 1995). In FIG. 8, quantitative results obtained from counting autophagic vacuoloes in 20 randomly chosen fields are displayed. While overexpression of wild-type PS1 showed a small, but statistically significant ($p \leq 0.13$), decrease in the mean number of autophagic vacuoles per field, expression of PS1Δ9 increased the number of autophagic vacuoles per filed over both untransfected N2a cells ($p \leq 0.04$) and over wild-type PS1 overexpressing N2a cells ($p \leq 0.004$). Again, the increased numbers of autophagic vacuoles seen in the N2a cells expressing the exon 9 deletion-mutant of PS1 further substantiates our observation that autophagy is increased in neurons by expression of mutant PS1.

Lysosomal System Abnormalities in Cells Expressing Mutant Presenilin-I

Figure 9:
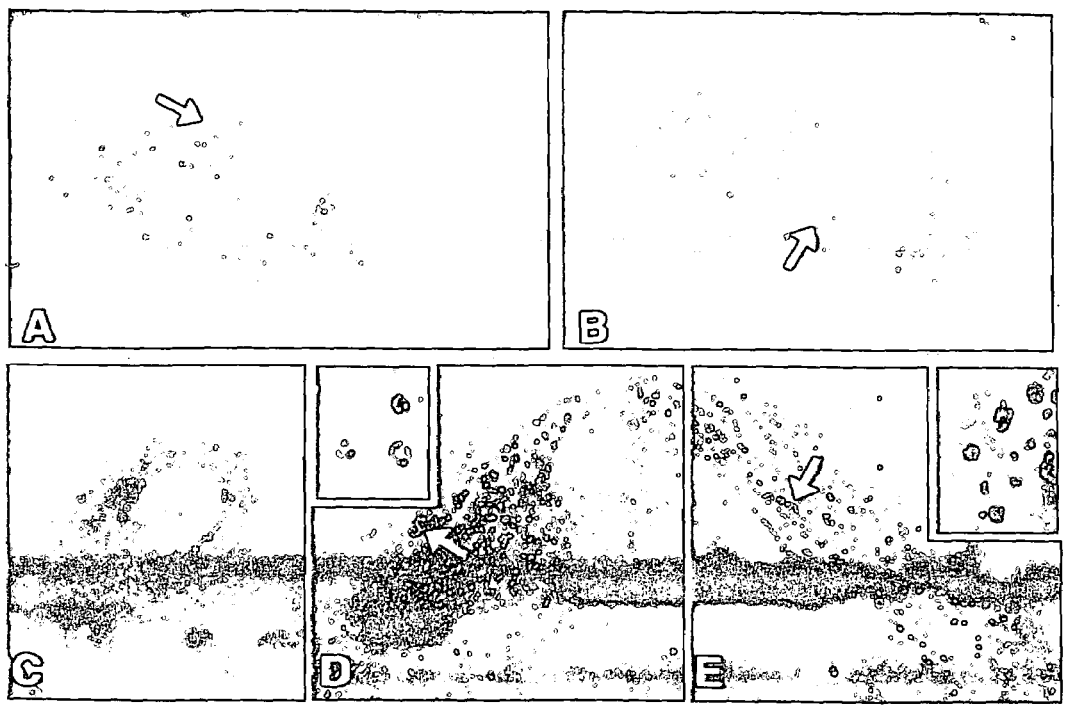
FIGS. 9A and 9B are photographs of hydrolase-positive lysosomes in control skin fibroblasts (FIG. 9A) and fibroblasts from an individual with a PS1 mutation (FIG. 9B).
FIGS. 9C and 9D are photographs of protein disulfide isomerase in control skin fibroblasts (FIG. 9C) and fibroblasts from an individual with a PS1 mutation (FIG. 9D).
FIG. 9E is a photograph of LAMP in fibroblasts from an individual with a PS1 mutation.

In studies using primary cultures of human skin fibroblasts from PS-FAD kindreds, we detected no alterations in early endosomal compartments, but observed an increase in the number of Cat D-positive compartments, comparable to our findings in PS-FAD cases (FIG. 9). Consistent with the possibility of a second, non-endosomal route to the lysosome, we found a number of enlarged vacuolar structures that were immunopositive for the ER-marker protein disulfide isomerase (PDI). The morphology of the PDI-positive compartments was similar to a subpopulation of large LAMP-2 (a lysosomal membrane protein) positive compartments in these same cells (FIG. 9).

One clue to why lysosomal activation may be enhanced by PS mutations is the predominant ER localization of PS. The important established role of the ER in autophagy (Holtzman, E., Plenum Press: Lysosomes, 1989), and the existence of an understudied degradative pathway from the ER and/or Golgi apparatus to the lysosome (Chen et al., J.

Cell Biol. 107:2149–2161, 1988; Noda and Farquhar, J. Cell Biol. 119:85–97, 1992), raise the possibility that PS mutations might increase autophagy and/or traffic through this alternative pathway—two scenarios that are supported by our findings.

The discovery of increased activity of pathways from the endoplasmic reticulum to lysosomes allows for the identification of compounds that are useful for the treatment of AD by assessing their ability to decrease activity of pathways from the endoplasmic reticulum to lysosomes.

We can test compounds for their ability to decrease the pathways from the ER to lysosomes in multiple model systems, including but not limited to: (i) cells in culture; (ii) primary neurons grown in culture; (iii) primary fibroblast lines derived from individuals with PS1 mutations; (iv) cells expressing mutant PS1 or PS2; (v) brains of normal mice; and (vi) brains of transgenic mice. Suitable human cultured fibroblast lines can be derived by antemortem skin biopsy from individuals carrying PS1 mutations (e.g., M233T, S169L, A246G, or M146L), as well as family-member control individuals. Example transfected murine cell lines include the previously described L cells (Kit et al., J. Virol. 1:238–240, 1967) expressing either wild-type human PS1 or the $PS1_{P117L}$ mutant (Wisniewski et al., Neuroreport 9:217–221, 1998) as well as the N2a cells. Other cell lines carrying mutant PS1 or PS2 alleles (e.g., M146L, M146V) are also suitable cell lines for the assays described herein. Alternatively, control and transgenic mice can be used to test the ability of a candidate compound to decrease activity of pathways from the endoplasmic reticulum to lysosomes in an animal model.

Measurements of Endoplasmic Reticulum to Lysosome Activity

Autophagy in the foregoing cell lines and animals can be assayed using any of a number of techniques, including the use of monodansyl-cadavarine (MDC), a fluorescent compound that specifically labels autophagic vacuoles (AV) but not early and late endosomes (Biederbick et al., Eur. J. Cell Biol., 66:3–14, 1995). EM morphometric analysis, as well as LM and EM immuno- and enzyme cytochemistry can also be used. We have previously defined AVs by EM as membrane-enclosed structures in which cellular organelles or cellular contents are identifiable (Cataldo and Nixon, Ann. N.Y. Acad. Sci. 679:87–109, 1993; Cataldo and Nixon, Trends Neurosci. 18:489–496, 1995). This definition excludes overlap with other membrane-delimited organelles of the secretory and endocytic pathways. The number and/or size of AVs will be quantified through morphometric analysis with standard statistical computations. The total area of the cell or region of interest is measured using a standardized grid, and the number of AVs counted and expressed per unit area. The ability of a candidate compound to reduce ER to lysosome conversion in the human or mouse cell lines can also be assayed by double immunofluorescence labeling experiments (Cataldo et al., Brain Res. 640:68–80, 1994) in which coincidence of ER markers and lysosomal markers will be used in cultured cells and in transgenic mouse brain. Coincidence of labeling can be determined using confocal microscopy. Antibodies to resident ER proteins that are useful in these assays include, but are not limited to, protein disulfide isomerase (PDI; StressGen, La Jolla, Calif.), calnexin (Hochstenbach, Hum. Cell 5:12–24, 1992), and BiP (StressGen) (Doms et al., Virology 193:545–562, 1993; Hammond and Helenius, Science 266:456–458, 1994). The lysosomal system is labeled using LAP enzyme cytochemistry or antibodies against, for example, Cat D, LAMP-1, or LAMP-2, the latter two being major glycoproteins of the lysosomal membrane (August and Hughes, J. Biol. Chem. 257:3970–3977, 1982; Mathews, J. Cell Biol. 118:1027–1040, 1992). ER to lysosome conversion can be further assayed by coupling EM morphology with EM immuno- and enzyme cytochemistry, the lumenal protein labeled by immunocytochemistry with, for example, DAB and osmium or by enzyme cytochemistry with lead precipitate, and the membrane protein labeled by immuno-gold. The following pairs of lumenal and membrane markers are provided as examples that are suitable for examination: LAP and calnexin; PDI and LAP; and Cat D and calnexin. Quantitation of compartments showing co-labeling for ER and lysosomal markers can be done as described above for EM morphometric analysis.

A recently identified rab-GTPase, rab24, may play a role in regulating ER/cis-Golgi transition to autophagic vacuoles. Epitope-tagged rab24 has been localized to ER-derived autophagic vacuoles (Barbosa et al., Genomics 30:439–444, 1995; Olkkonen et al., J. Cell Sci. 106:1249–1261, 1993). We have isolated a cDNA encoding human rab24 and inserted this in-frame into a bacterial GST-fusion protein vector (pGEX-4T; Pharmacia, Piscataway, N.J.), which has been expressed in bacteria. To produce antibodies to rab24, we immunize rabbits and test serum for immunoreactivity against GST, GST-rab24, rab24 released from the GST by thrombin digestion, and GST-rab5. Affinity purified antibodies can be characterized using a well established in vitro system where amino acid starvation of hepatocytes induces a massive upregulation of cellular autophagy (Seglen et al., J. Cell Biol. 99:435–444, 1984; Seglen et al., Semin. Cell Biol. 1:441–448, 1990). The coincidence of rab24 immunoreactivity and morphologic and immunological indices of autophagy establish the specificity of the rab24 antibody. Using these antibodies, rab24 expression can be used in the assay of drugs in transgenic mice or human or mouse as described above.

Autophagy Inhibitors Reduce Aβ Production and Increase tau Expression in Murine Neuroblastoma Cells Based on our finding that increased activity of pathways from the ER to lysosomes is increased in AD, we hypothesize that compounds that decrease this activity are very likely to decrease Aβ formation. We tested this directly by incubating cultured cells in the presence or absence of two different autophagy inhibitors: 3MA or leucine and histidine (Seglen and Gordon, Proc. Natl. Acad. Sci. USA 79:1889–1892, 1982; Seglen and Gordon, J. Cell Biol. 99:435–444, 1984).

Figure 10:
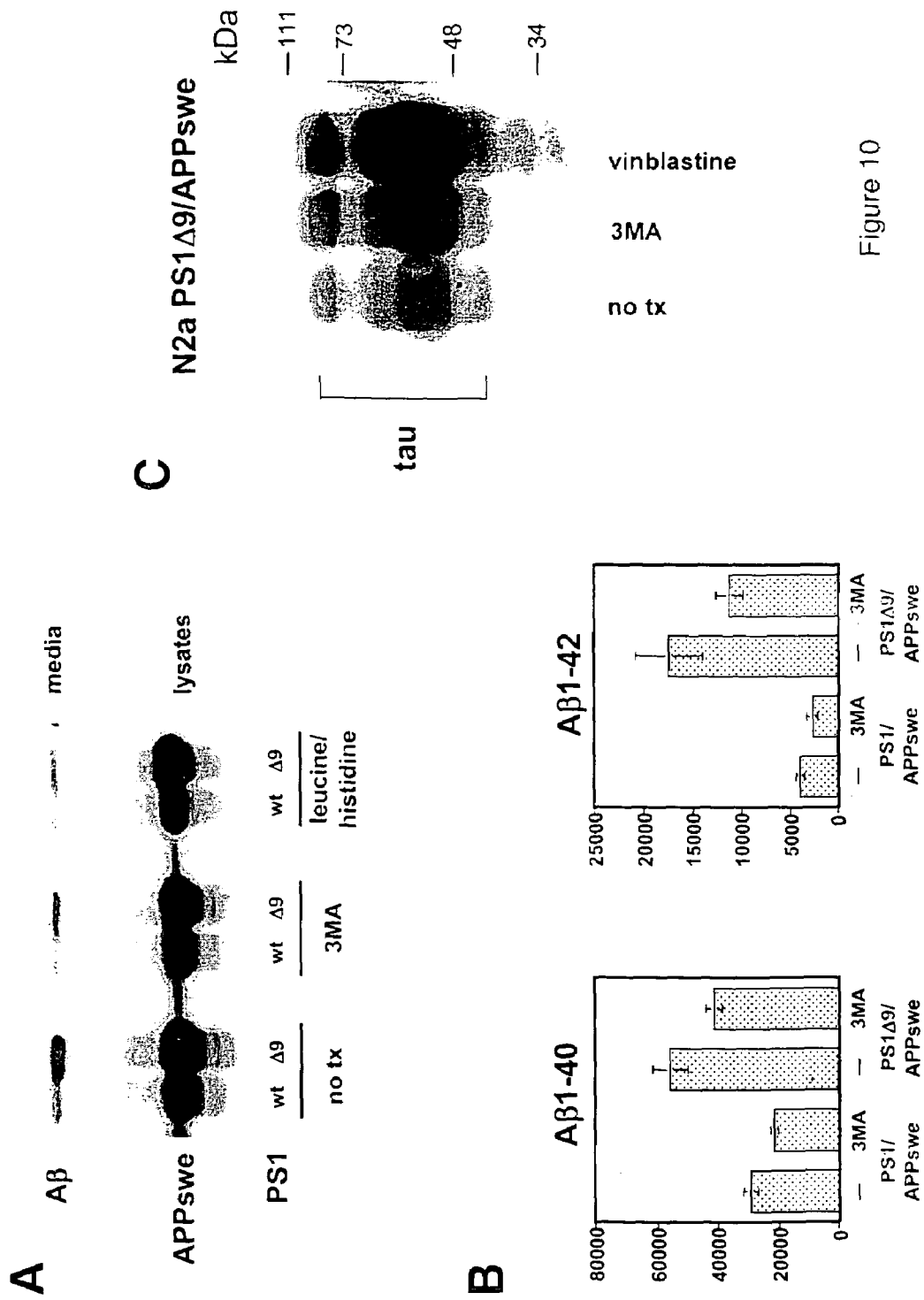
FIG. 10A is a photograph of an autoradiograph showing Aβ generation is decreased in neuroblastoma cells following treatment with 3MA and leucine/histidine.
FIG. 10B is a schematic illustration showing by ELISA decreased Aβ secretion into the growth media following treatment of N2a cells with 3MA.
FIG. 10C is a photograph of a Western blot showing increased tau protein levels in 3MA-treated and vinblastine-treated PS1Δ9/APPswe N2a cells.

Murine neuroblastoma N2a cells expressing the Swedish mutant of APP and wild-type PS1 (APPswe/PS1 wt) and N2a cells expressing APPswe/PS1Δ9 (i.e., APPswe and PS1 in which exon 9 has been deleted (Δ9)) were grown in the absence or presence of 3MA (10 mM) or leucine and histidine (10 mM each). Cells were then metabolically labeled for four hours, again in the absence or presence of autophagy inhibitors. The growth medium was collected and subjected to immunoprecipitation with an anti-Aβ monoclonal antibody that recognizes both Aβ1-40 and Aβ1-42. Labeled Aβ was resolved by SDS-PAGE and fluorography (FIG. 10A). N2a cells produce little endogenous Aβ. Expression of human APPswe greatly increased the amount of Aβ secreted. Inhibiting autophagy with either autophagy inhibitor reduced the amount of Aβ secreted in APPswe/PS1 wt expressing cells as well as in the APPswe/PS1Δ9 expressing cells (FIG. 10A), top panel, but did not affect the amount of full-length APP immunoprecipitated from cell lysates with C-terminal antibody (FIG. 10A, bottom panel).

In a second set of experiments, N2a cells expressing APPswe/PS1 wt or APPswe/PS1Δ9 were incubated either in the presence or absence of 5 mM 3MA (FIG. 10B). Conditioned medium was collected and pooled from two plates and spun at 1000×g to remove cells and cellular debris. The amount of secreted Aβ was then determined using ELISA. In both APPswe/PS1 wt and APPswe/PS1 Δ9 N2A cells incubated in the presence of 3MA, there was a reduction of Aβ1-40 and Aβ1-42 in the conditioned medium (FIG. 10B). While the decrease was greatest in the N2A cells expressing mutant PS1, we found a significant decrease of approximately 20% or great for both Aβ species in both the wild-type and Δ9 PS1 expressing lines.

Additionally, we have found that inhibiting autophagy with 3MA or preventing fusion of nascent autophagic vacuoles with lysosomes by vinblastine treatment (50 μM; Kopitz et al., J. Cell Biol. 111:941–953) increased tau protein levels in N2a cells expressing APPswe/PS1Δ9 (FIG. 10C). Tau protein levels were increased by approximately 2 times in 3MA-treated N2a cells, and 2.5 times in vinblastine-treated cells. We have also shown an approximate doubling in tau levels following treatment with leucine and histidine (10 mM each).

Several studies have recently raised the possibility that abnormal forms of tau is metabolized in lysosomes, which is consistent with our hypothesis that organelle turnover by autophagy might involve tau-containing structures. There are numerous assays for tau known in the art. For example, the processing of tau by immunocytochemistry and Western blot analysis is performed using an antibody that recognizes both phosphorylated and non-phosphorylated forms (Adamec et al., Brain Res. 757:93–101, 1997). Abnormal tau conformation and byperphosphorylated tau is examined using suitable monoclonal antibodies (e.g., MC1 (Jicha et al., J. Neurosci. Res. 48:128–132) and AT8 (Innogenetics, Gent, Belgium)). EM analysis can be performed to characterize cytoskeletal changes in neurons (Nixon, Bioessays 20:798–807, 1998).

Figure 11:
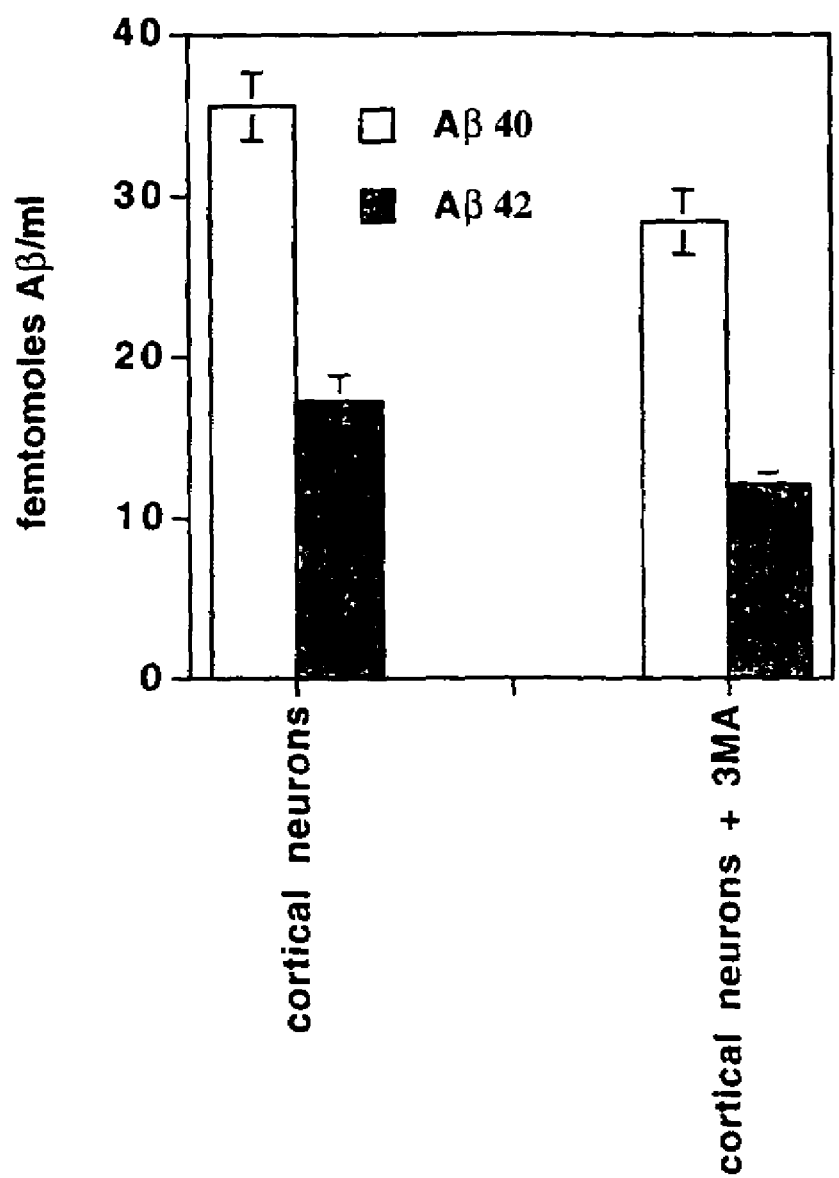
FIG. 11 is a schematic illustration showing a reduction in Aβ secretion into the media following 3MA treatment of primary cortical neurons isolated from normal mice.

We have confirmed this effect of the autophagy inhibitor 3MA on Aβ production in primary cortical neuronal cultures derived from normal mouse embryos (FIG. 11). Following a media change, cultures were incubated in the presence or absence of 3MA for six hours. This media was collected and the levels of Aβ40 and Aβ42 determine by ELISA. 3MA treatment reduced the amount of both Aβ species secreted by the neurons into the media by approximately 20%. This finding indicates that affecting autophagy may have therapeutic value in all forms of AD, not just those resulting from mutations within the presenilin or APP genes. These data indicate that autophagy is a major pathway for the generation of Aβ and that inhibitors of the autophagy pathway, such as 3MA, leucine and histidine, or vinblastine, may significantly reduce the amount of Aβ secreted from neurons, while increasing tau protein levels.

Early Diagnosis of Alzheimer's Disease

The invention described herein also allows for early diagnosis of AD by the assessment of activity of pathways from the ER to lysosomes in a sample from a patient, compared to a person who does not have AD. The assays described herein are all applicable for this method of diagnosis. The sample can be a cell biopsy, or it can be a biological fluid such as CSF or blood.

Test Compounds and Extracts

In general, compounds are identified from large libraries of both natural product extracts and synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to reduce activity of pathways from the endoplasmic reticulum to lysosomes, further fractionation of the positive lead extract is necessary to isolate chemical constituents responsible for the observed effect. Thus, the goal of the extraction, fractionation, and purification process is the careful characterization and identification of a chemical entity within the crude extract having the desired activity. Methods of fractionation and purification of such heterogenous extracts are known in the art. If desired, compounds shown to be useful agents for the treatment of lysosomal abnormalities are chemically modified according to methods known in the art.

Uses

For therapeutic uses, the compounds, compositions, or agents identified using the methods disclosed herein may be administered systemically, for example, formulated in a pharmaceutically-acceptable buffer such as physiological saline. Treatment may be accomplished directly, e.g., by treating the animal with antagonists which disrupt, suppress, attenuate, or neutralize the biological events associated with AD. Preferable routes of administration include, for example, inhalation or subcutaneous, intravenous, interperitoneally, intramuscular, or intradermal injections which provide continuous, sustained levels of the drug in the patient. Treatment of human patients or other animals will be carried out using a therapeutically effective amount of an agent in a physiologically-acceptable carrier. Suitable carriers and their formulation are described, for example, in Remington's *Pharmaceutical Sciences* by E. W. Martin. The amount of the compound to be administered varies depending upon the manner of administration, the age and body weight of the patient, and with the type of disease and extensiveness of the disease. A compound is administered at a dosage that decreases activity of the pathways from the endoplasmic reticulum to lysosomes. For example, for systemic administration a compound is administered typically in the range of 0.1 ng–10 g/kg body weight.

Methods

Primary Neuronal Cell Culture

Dissected embryonic cortical tissue from Sprague-Dawley rat embryos (18d gestation) or mouse embryos (17d gestation) is rinsed with calcium/magnesium-free Hanks buffered saline solution and resuspended in 5.0 ml 0.125% trypsin and 0.5 mM EDTA at 37° C. The suspension is triturated by gentle pipeting and incubated in a shaking water bath for 10 min at 37° C. Trypsin is quenched and the cells are plated at $1.5 \times 10^6$ cells/mL on polylysine coated plates and cultured at 37° C. in 5% $CO_2$ in B27/Neurobasal medium (Gibco/BRL, Gaithersburg, Md.) containing 0.0015% fluorodeoxyuridine (FUDR), giving cultures that are >95% neuronal.

Immunocytochemistry and Digital Confocal Microscopic Analysis

Sections of aldehyde-fixed human or transgenic mouse brain, or cultured cells are reacted as previously described (Cataldo et al., Neuron 14:671–680, 1995; Cataldo et al., J. Neuropathol. Exp. Neurol 55:704–715, 1996; Cataldo, et al., Adv. Exp. Med. Biol., 389:271–280, 1996; Cataldo et al., J. Neurosci. 16:186–199, 1996; Cataldo et al., Brain Res. 513:181–192, 1990; Nixon et al., Ann N.Y. Acad. Sci. 679:87–109, 1993; Nixon and Shea, Cell Motil. Cytoskeleton 22:81–91,1992).

Enzyme Cytochemistry

For demonstration of acid phosphatase activity, 0.0015M cytidine-3i,5i-cyclic monophosphate (Sigma) in 0.1 M tris-maleate buffer, pH 5.5, is used as substrate (A. Novikoff, Lysosomes in the physiology and pathology of cells. Little Brown and Co., Boston, pp. 36, 1963; A. Novikoff, Lysosomes in nerve cells. Elsevier Publishing Co., N.Y., pp. 319, 1967) for glucose-6-phosphatase activity, 0.00175 M glucose-6-phosphate (Sigma Chemicals, St. Louis, Mo.) in 0.1 M Tris-maleate buffer, pH 6.8, is used (Broadwell et al., J. Histochem. Cytochem. 31:1077–1088, 1983; Broadwell et al., J. Histochem. Cytochem. 31:818–822, 1983). Incubation proceeds at 37° C. for 30–90 min. Enzymatically released phosphate is trapped as a lead precipitate visualized directly in electron microscopy and after conversion to a lead sulfide in light microscopy.

In the brains of transgenic mice overexpressing APPswe, PS1 wt, $PS1_{M146L}$ (or combinations thereof) in the presence and absence of candidate compounds, we assess the LS using sMPR (Valenzano et al., Anal. Biochem. 209:156–162, 1993); antibodies specific for Cat D and cystatin C; an in situ enzyme assay for LAP (Novikoff, Elsevier Publishing Co., N.Y., pp. 319, 1967); and antibodies specific for MPR46 and MPR215 (Cataldo et al., J. Neurosci. 17:6142–6151, 1997). Tissue sections from the selected anatomical regions are processed for immuno- and enzyme-cytochemistry as previously described (Cataldo et al., J. Neuropathol. Exp. Neurol. 55:704–715, 1996; Cataldo et al., Adv. Exp. Med. Biol. 389:271–280, 1996; Cataldo et al., Brain Res. 640:68–80, 1994). In addition to immunochemistry, these markers are used in Western blot analysis. Additional EP and LS markers known to those in the art can also be useful in the present method.

LAP activity in brain homogenates is determined using a colorimetric assay based on the hydrolysis of 10 mM p-nitrophenyl phosphate in 0.1 M sodium citrate, pH 4.5 (Saftig et al., J. Biol. Chem. 272:18628–18635, 1997). Aβ levels and β-amyloid burden are determined by a quantitative ELISA assay and by image analysis of β-amyloid plaque density, respectively. Indices of LS upregulation include an increase in lysosome numbers and density of lysosome-specific labels in neurons; increases in lysosomal enzyme activity and/or the levels of lysosomal hydrolases detected by Western blot analysis; and changes in lysosomal enzyme distribution, including the presence of lysosomal hydrolases in the secretory pathway, in endocytic compartments, and associated extracellularly with plaque. We can examine proteolytic (e.g. Cat D), and non-proteolytic (LAP) lysosomal hydrolases, and the proteins responsible for targeting most acid hydrolases to the lysosome (MPR215, MPR46), and the endogenous inhibitor cystatin C.

Isolation and Assay of Cathepsins

Cat D is assayed as pepstatin-inhibitable activity in the TCA soluble fraction prepared from brain homogenate according to Nixon & Marotta (Marotta, C. A. and Nixon, R. A., J. Neurochem, 43: 507–516, 1984), using $^{14}C$-labelled methemoglobin. Cat B and Cat L are assayed according to the protocol of Barret and Kirschke (Barrett, A. J. and Kirschke, H., Methods Enzymol, 80: 535–561, 1981) by measuring amc released from Z-Arg-Arg-amc (specific for Cat B) and Z-Phe-Arg-amc (specific for Cat B and L). Immunoreactive Cat B and D are measured by Western blot analysis as described (Mohan and Nixon, J. Neurochem. 64:859–866, 1995) using polyclonal antibodies raised against the mature forms of Cat D and Cat B as probes.

Aβ ELISA Methods

The Aβ sandwich ELISA is generally known to those skilled in the art, with both Aβ ELISA kits (Biosource International, Camaville, Calif.) and appropriate antibodies (e.g., 4G8, 6E10; Saneteck PLC, Napa, Calif.) commercially avaliable.

For the Aβ sandwich ELISA, Nunc-Immuno Plates (Nunc A/S, Roskilde, Denmark) were coated overnight using 4° C. using antibodies specific for Aβ40 or Aβ42 in 100 mM bicarbonate buffer, pH 9.6. Remaining protein binding sites were blocked by incubating with 1% Block Ace (Yukijirushi Milk, Sapporo Japan) in PBS for 4 hours at room temperature. 10% (w/v) homogenates were prepared from a hemibrain in 20 MM Tris, 250 mM sucrose, 1 mM EDTA, 1 mM EGTA, protease inhibitors, pH 7.4, and stored frozen at −70° C. Immediately prior to being loaded on the ELISA, 1 ml of the brain homogenate was extracted in diethylamine (Sigma, St. Lousi, Minn.) by adding an equal volume of 0.4% DEA in 100 mM NaCl, re-homogenized and centrifuged for 1 hour at 100,000×g. The supernatant was collected, neutralized with 0.1 volume 0.5 M Tris, pH 6.8, and loaded in duplicate wells both neat and diluted 1:2 in EC buffer (20 mM Na phosphate, 2 mM EDTA, 400 mM NaCl, 0.2% BSA, 0.4% Block Ace, 0.95% CHAPS). This DEA extraction protocol has been shown to efficiently recover immunoreactive Aβ from mouse brain homogenates and leave both full-length and sAPP in the 100,000×g pellet (Savage et al., 1998). Alternatively, conditioned media collected from cells was loaded neat and 1:2. Aβ-40 and Aβ-42 peptide standards were purchased from American Peptide Co. (Sunnyvale, Calif.), stored at −70° C., and diluted in EC buffer immediately prior to use. ELISA plates were incubated overnight with 4° C. with samples and standards. Aβ was detected by incubating for 4 hours at room temperature with an HRP-conjugated anti-Aβ antibody in 20 mM Na phosphate, 2 mM EDTA, 400 mM Nacl, 1.0% BSA. ELISA plates were developed using a color reaction (ABTS Peroxide Substrate System, Kirkegaard & Perry, Gaithersburg, Md.) and the $OD_{450}$ read.

Additional Methods

A compound that decreases the activity of pathways from the ER to lysosomes can be further tested for AD-like abnormalities in physiology, anatomy, or behavior using assays known to those skilled in the art, including those described in U.S. Pat. No. 5,877,399, hereby incorporated by reference.

OTHER EMBODIMENTS

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. A method for identifying a candidate compound as a compound that may be useful for the treatment of neuronal atrophy-associated dementia, said method comprising the steps of:
   (a) providing a first cell having a defect in a non-endosomal route to lysosomes;
   (b) contacting said first cell with a candidate compound; and
   (c) detecting a decrease in the level of an autophagic marker in said first cell relative to the level of said autophagic marker in a second cell of the same type having a normal non-endosomal route to lysosomes and not contacted with said candidate compound, wherein said decrease identifies said candidate compound as a compound that may be useful for the treatment of neuronal atrophy-associated dementia.

2. The method of claim 1, wherein said first cell comprises a mutation in PS1, PS2, or APP.

3. The method of claim 1, wherein said decrease in the level of an autophagic marker is measured by assaying the number of autophagic vacuoles.

4. The method of claim 1, wherein said method is carried out in vitro.

5. The method of claim 1, wherein said autophagic marker is monodansylcadaverine or rab24.

* * * * *

UNITED STATES PATENT AND TRADEMARK OFFICE
CERTIFICATE OF CORRECTION

PATENT NO. : 7,090,987 B1
APPLICATION NO. : 09/561582
DATED : August 15, 2006
INVENTOR(S) : Nixon et al.

Page 1 of 1

It is certified that error appears in the above-identified patent and that said Letters Patent is hereby corrected as shown below:

Column 4,
    Line 4, replace "compare d" with --compared--;
    Line 15, replace "(FIG. 5A)*and*" with --(FIG. 5A) and--;
    Line 32, replace "untrasfected" with --untransfected--.

Column 8,
    Line 37, replace "vaculoes" with --vacuoles--;
    Line 40, replace "filed" with --field--.

Column 12,
    Line 25, replace "oceangraphics" with --oceanographics--;
    Line 48, replace "heterogenous" with --heterogeneous--.

Column 14, Lines 44 and 45, replace "coated overnight using 4° C. using antibodies" with --coated overnight using antibodies--.

Column 15, Lines 1 and 2, replace "incubated overnight with 4° C. with samples" with --incubated overnight with samples--.

Signed and Sealed this

Thirteenth Day of March, 2007

JON W. DUDAS
*Director of the United States Patent and Trademark Office*